United States Patent
Graziani et al.

(10) Patent No.: US 9,211,083 B2
(45) Date of Patent: *Dec. 15, 2015

(54) SYSTEMS AND METHODS FOR MAGNETIC MATERIAL IMAGING

(71) Applicant: General Electric Company, Schenectady, NY (US)

(72) Inventors: Michael Dominic Graziani, Niskayuna, NY (US); Thomas Kwok-Fah Foo, Niskayuna, NY (US); Luca Marinelli, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 144 days.

This patent is subject to a terminal disclaimer.

(21) Appl. No.: 14/025,509

(22) Filed: Sep. 12, 2013

(65) Prior Publication Data
US 2015/0073264 A1 Mar. 12, 2015

(51) Int. Cl.
*A61B 5/06* (2006.01)
*A61B 5/05* (2006.01)

(52) U.S. Cl.
CPC .............. *A61B 5/062* (2013.01); *A61B 5/0515* (2013.01)

(58) Field of Classification Search
CPC ......... A61B 5/062; A61B 5/064; G01N 27/72
See application file for complete search history.

(56) References Cited

U.S. PATENT DOCUMENTS

| | | |
|---|---|---|
| 2004/0097803 A1 | 5/2004 | Panescu |
| 2010/0063385 A1 | 3/2010 | Garibaldi et al. |
| 2010/0168553 A1 | 7/2010 | Martel et al. |
| 2011/0230758 A1 | 9/2011 | Eichler |
| 2011/0237928 A1 | 9/2011 | Rahmer et al. |
| 2011/0246103 A1 | 10/2011 | Rahmer et al. |
| 2011/0295108 A1 | 12/2011 | Cox et al. |

(Continued)

FOREIGN PATENT DOCUMENTS

| | | |
|---|---|---|
| WO | 2008060589 A2 | 5/2008 |
| WO | 2012098551 A1 | 7/2012 |

OTHER PUBLICATIONS

Merdes, "Locating a catheter transducer in a three-dimensional ultrasound imaging field", IEEE Trans Biomed Eng, vol. 48, Issue 12, pp. 1444-1452, Dec. 2001.

(Continued)

*Primary Examiner* — Michael Rozanski
(74) *Attorney, Agent, or Firm* — The Small Patent Law Group LLC; Christopher R. Carroll (57) ABSTRACT

Magnetic material imaging (MMI) system including a first array of elongated wire segments that extend substantially parallel to an imaging plane. The imaging plane is configured to extend through a region-of-interest (ROI) of an object. The MMI system also includes a second array of elongated wire segments that extend substantially parallel to the imaging plane. The first and second arrays of wire segments are spaced apart with the imaging plane therebetween. The first and second arrays of wire segments form segment pairs. Each segment pair includes a wire segment of the first array and a wire segment of the second array, wherein the wire segments substantially coincide along a segment plane. The MMI system also includes a phase-control module configured to control a flow of current through the wire segments of the segment pairs to generate and move a one-dimensional field free region (1D FFR) within the imaging plane.

20 Claims, 4 Drawing Sheets

(56) References Cited

U.S. PATENT DOCUMENTS

| | | |
|---|---|---|
| 2012/0157823 A1 | 6/2012 | Gleich |
| 2014/0159712 A1 | 6/2014 | Graziani et al. |
| 2014/0275962 A1 | 9/2014 | Foo et al. |

OTHER PUBLICATIONS

Gleich et al., "Tomographic imaging using the nonlinear response of magnetic particles", Nature 435, pp. 1214-1217, Jun. 30, 2005.

Lederman, "Cardiovascular Interventional MRI", Circulation, vol. 112, Issue 19, pp. 3009-3017, Nov. 8, 2005.

Weizenecker et al., "Magnetic particle imaging using a field free line", Journal of Physics D: Applied Physics, vol. 41, Issue 10, 2008.

Goodwill at al., "Narrowband magnetic particle imaging", IEEE Trans Med Imaging, vol. 28, Issue 8, pp. 1231-1237, Aug. 2009.

Loke et al., "Magnetic Tracking System for Radiation Therapy", IEEE Transactions on Biomedical Circuits and Systems, vol. 4, Issue 4, pp. 223-231, Aug. 2010.

Rahmer et al., "Rapid 3D in vivo Magnetic Particle Imaging with a Large Field of View", 19th Annual Meeting International Society for Magnetic Resonance in Medicine, pp. 3285, 2011.

Goodwill et al., "Multidimensional x-space magnetic particle imaging", IEEE Trans Med Imaging, vol. 30, Issue 9, pp. 1581-1590, Sep. 2011.

Konkle et al., "Experimental 3D X-Space Magnetic Particle Imaging Using Projection Reconstruction", Magnetic Particle Imaging Springer Proceedings in Physics, vol. 140, pp. 243-247, 2012.

Haegele et al., "Visualization of Instruments for Cardiovascular Intervention Using MPI", Magnetic Particle Imaging Springer Proceedings in Physics, vol. 140, pp. 211-215, 2012.

Wojtczyk et al., "Visualization of Instruments in interventional Magnetic Particle Imaging (iMPI): A Simulation Study on SPIO Labelings", Magnetic Particle Imaging Springer Proceedings in Physics, vol. 140, pp. 167-172, 2012.

Goodwill et al., "Projection X-Space Magnetic Particle Imaging", IEEE Transactions on Medical Imaging, vol. 31, No. 5, May 2012.

Vogel et al., "Slicing Frequency Mixed Traveling Wave for 3D Magnetic Particle Imaging", Magnetic Particle Imaging, SPPHY 140, pp. 231-235.

SYSTEMS AND METHODS FOR MAGNETIC MATERIAL IMAGING

BACKGROUND

In some medical procedures, surgical instruments may be tracked by imaging the position of the instrument in real-time with respect to the surrounding anatomy. For example, in one conventional method, a position of a catheter is continuously monitored by two-dimensional (2D) x-ray fluoroscopy, and the surrounding tissue (e.g., vasculature) is visualized with contrast agent injections. Because of the continuous x-ray imaging, however, the total dose of ionizing radiation received by the patient during this procedure can be a concern. In addition, nearby personnel are required to wear lead aprons to limit exposure to the ionizing radiation.

Other imaging modalities have been proposed for tracking surgical instruments, but these imaging modalities have certain problems or drawbacks such as high cost of equipment and/or operation, long acquisition times, substantial hardware or equipment modifications, or poor quality of images. For example, magnetic resonance imaging (MRI) has been used to track surgical instruments. Generally, MRI can provide high resolution 3D images with excellent contrast of the surrounding anatomy. However, surgical tracking using MRI can be expensive, may have a low acquisition rate, and may provide limited access to the patient compared to X-ray fluoroscopy. Moreover, any surgical instrument used in the procedure must be non-ferrous, potentially limiting the instruments available to the surgeon.

Ultrasound is another non-invasive imaging technology that has been applied to catheter tracking. One challenge with ultrasound tracking is that the catheter operates as a specular reflector. Therefore, it is often necessary to modify the catheter in some way, such as placing a transducer on the tip, in order to visualize the catheter position in ultrasound. This can add to the bulk and cost of the instrument.

Accordingly, systems and methods for tracking surgical instruments without using imaging modalities that can be harmful to the patient or require costly equipment are generally desired. Magnetic particle imaging (MPI) is a recently developed imaging modality in which a spatial distribution of magnetic particles can be determined. For example, MPI is capable of imaging a distribution of superparamagnetic iron oxide particles (SPIOs) with a relatively high sensitivity, high spatial resolution, and high imaging speed. In particular, MPI detects the magnetization change caused when a sensitive region passes through the sample (e.g., a region in which there is little or no magnetic field surrounded by a larger saturating field). Unlike other imaging modalities, MPI is free of ionizing radiation. However, the known MPI systems are directed to imaging a single point and moving that point relative to the object-of-interest. With a sensitive point configuration, image acquisition is inherently three dimensional which can therefore result in significantly long acquisition times. Accordingly, a system for acquiring three dimensional images of magnetic material in less time than conventional MPI systems is desired.

BRIEF DESCRIPTION

In one embodiment, a magnetic material imaging (MMI) system is provided that includes a first array of elongated wire segments that extend substantially parallel to an imaging plane. The imaging plane is configured to extend through a region-of-interest (ROI) of an object. The MMI system also includes a second array of elongated wire segments that extend substantially parallel to the imaging plane. The first and second arrays of wire segments are spaced apart with the imaging plane therebetween. The first and second arrays of wire segments form segment pairs. Each segment pair includes a wire segment of the first array and a wire segment of the second array, wherein the wire segments substantially coincide along a segment plane. The MMI system also includes a phase-control module that is configured to control a flow of current through the wire segments of the segment pairs to generate and move a one-dimensional field free region (1D FFR) within the imaging plane. Each of the segment pairs has a time-varying phase that is offset with respect to the phase of at least one other segment pair. The MMI system also includes a detection assembly positioned relative to the ROI to detect changes in magnetization of magnetic material located proximate to the 1D FFR.

In another embodiment, a magnetic material imaging (MMI) system is provided that includes a first field-generating unit having an assembly housing and a first array of elongated wire segments held by the assembly housing of the first field-generating unit. The MMI system also includes a second field-generating unit having an assembly housing and a second array of elongated wire segments held by the assembly housing of the second field-generating unit. The first and second arrays of wire segments extend substantially parallel to a common imaging plane that extends through a region-of-interest (ROI) of an object. The first and second field-generating units are located on opposite sides of the imaging plane. The MMI system also includes a phase-control module that is configured to control a flow of current through the wire segments of the first and second arrays to generate and move a one-dimensional field free region (1D FFR) within the imaging plane. Each of the wire segments has a phase that is offset with respect to the phase of at least one other wire segment. The MMI system also includes a detection assembly positioned relative to the ROI to detect changes in magnetization of magnetic material located proximate to the 1D FFR.

In yet another embodiment, a method of imaging a region-of-interest (ROI) in a patient through magnetic material imaging (MMI) is provided. The method includes providing a first array of elongated wire segments and a second array of elongated wire segments. The wire segments of the first and second arrays extend substantially parallel to an imaging plane that is positioned between the first and second arrays. The method also includes generating a 1D FFR based on current flowing through the wire segments of the first and second arrays and based on positions of the wire segments relative to one another. The method also includes controlling phases of the current flowing through the wire segments to move the 1D FFR within the imaging plane. The method also includes detecting changes in magnetization of magnetic material located proximate to the 1D FFR in a ROI of a patient.

DETAILED DESCRIPTION

Embodiments described herein include systems and methods for imaging magnetic material in a spatial region. The systems and methods are based on a magnetic material imaging (MMI) modality, which may also be referred to as magnetic material tracking (MMT). MMI (or MMT) may be used to image a distribution of magnetic material (e.g., superparamagnetic iron oxide particles (SPIOs)) within the spatial region, such as within a patient's body. MMI detects changes in magnetization of the magnetic material that is proximate to a sensitive region (e.g., a field free point (FFP) or field free region (FFR)) that is generated by the MMI system. As used herein, the term "proximate to" includes the magnetic material being directly within or overlapping the sensitive region and also the magnetic material being suitably near the sensitive region. Magnetic material is suitably near the sensitive region if an MMI system is capable of detecting changes in magnetization of the magnetic material for the purpose of imaging a region-of-interest (ROI) using MMI.

More specifically, magnetic material, such as SPIOs, can be spatially localized by applying a time-varying external magnetic field that has a designated or predetermined geometry. When exposed to the external magnetic field, domains in the magnetic material begin to align and the magnetization of the sample increases. Once all of the domains of the magnetic material are aligned with the external field, the sample is said to be "saturated" and further increases in the applied field produce minimal or undetectable changes in the magnetization. On the other hand, if a region of the applied field is relatively small such that the magnetic material is not saturated, perturbations in the region of the applied field may produce changes in magnetization, which can induce a measurable signal. For example, the measurable signal may be represented by a change in voltage or current detected by a detection assembly. Thus, if the applied field is configured to have one or more high-field regions, wherein the magnetic material is saturated, and one or more low-field regions, wherein perturbations may produce changes in magnetization, an image can be constructed by moving (e.g., sweeping, scanning, rastering) the low-field region(s) throughout the object and detecting the changes in magnetization.

Accordingly, embodiments set forth herein are configured to generate one or more low-field regions for MMI. For example, embodiments may be configured to generate one or more one-dimensional (1D) FFRs and detect changes in magnetization of the magnetic material proximate to the 1D FFR(s). As used herein, a 1D FFR may be an elongated sensitive region that is substantially linear (e.g., straight) or curved between two different point regions. By way of example only, the 1D FFR may have a cross-section transverse to the length of the 1D FFR that is substantially uniform in size (e.g., about 0.5 mm$^2$ to about 5.0 mm$^2$). The 1D FFR may be formed by an arrangement of wire segments. As used herein, a "wire segment" represents a portion of a wire or wires used to generate an external magnetic field that may be combined with other external magnetic field(s) to generate the 1D FFR. In some cases, there may be other portions of the wire or wires that provide external magnetic field(s) that are not used to generate the 1D FFR.

In some embodiments, a first array of wire segments may be located on one side of an imaging plane and a second array of wire segments may be located on another side of the imaging plane. In some embodiments, the wire segments may form segment pairs in which each segment pair includes at least one wire segment from the first array and at least one wire segment from the second array. In particular embodiments, two wire segments form a single segment pair. The two wire segments may extend parallel to each other such that the wire segments extend within a common plane (referred to as segment plane or segment-pair plane).

The wire segments are configured to have a varying (e.g., sinusoidal) current flowing therethrough and may be positioned relative to one another to form a movable 1D FFR between the first and second arrays. For example, current flowing through adjacent segment pairs may be varying such that the phases of the currents are offset with respect to each other. By controlling the flow of current through the wire segments (or through the segment pairs), a movable 1D FFR can be generated.

In particular embodiments, the movable 1D FFR rotates about an axis of rotation. The axis of rotation may be perpendicular or orthogonal to the imaging plane. However, in other embodiments, the movable 1D FFR may be moved in other manners. For example, the 1D FFR may be shifted within the imaging plane or may be shifted in a direction orthogonal to the imaging plane.

In certain embodiments, the wire segments of a designated array have a hub-and-spoke configuration in which the wire segments of the designated array generally cross one another at a common point region (e.g., pivot-point region). With such a configuration, the current flowing through the wire segments may be controlled to generate a movable 1D FFR that, for example, rotates about an axis.

The current flowing through the wire segments or the segment pairs may be controlled (e.g., increased, decreased, or otherwise modified) to position and reposition the 1D FFR within the ROI. By adjusting the current, the system can move (e.g., raster, sweep, rotate, and the like) the 1D FFR and obtain image data. The image data may be based on a measureable induced voltage or a measurable change in current caused by the changes in magnetization. The image data may then be used to generate viewable images (e.g., 2D images, 3D images, or 4D images). In some embodiments, data acquisition and image generation occur in real-time thereby enabling a clinician or other qualified individual to use the imaging system for medical purposes. For example, the MMI system may be used to visualize an instrument, which has magnetic material and has been inserted into the patient, during a medical procedure (e.g., surgery). As one specific example, the MMI system may be used during a cardiac catheterization procedure in which a catheter that includes magnetic material is imaged or tracked by the MMI system while the catheter is within a patient's body. The magnetic material may be distributed throughout the catheter or located at predefined regions (e.g., tip, edges, and the like). In some cases, the MMI system may be used with other imaging modalities, such as x-ray. In that case, MMI images may be combined with x-ray images to co-register the catheter position with anatomy in real-time.

One or more embodiments may be particularly suitable for tracking an instrument within a patient. The instrument may be doped or otherwise integrated with the magnetic material in a manner that minimizes exposure of the magnetic material to the patient. In such cases, the type of magnetic material integrated with the instrument may be configured in a manner that renders the instrument more easily detectable through MMI. For example, the size of the magnetic particles may be greater and/or smaller than the magnetic particles that are conventionally used or the composition of the magnetic particles may provide greater or smaller magnetic moments. In some cases, different magnetic materials (e.g., differing in particle size and/type/or composition) may provide characteristic signatures that enable a system to distinguish the different magnetic materials.

Although particular embodiments may be suitable for tracking instruments in a patient, embodiments set forth herein are not limited to the tracking of instruments. For example, in some cases, the MMI systems and methods described herein may be used to image magnetic material that has been injected into a patient. In other embodiments, the MMI systems and methods described herein may be used to image magnetic material that is found in an inanimate object (e.g., luggage, shipping containers, etc).

In some embodiments, the MMI system has a bi-planar, "c-arm" geometry. In some embodiments, the MMI system is capable of 2D projection imaging. For example, the images may be of a surgical instrument that is integrated with (e.g., doped) or otherwise affixed to magnetic material. The images may also be of a patient's tissue or otherwise localized region of the patient's anatomy. Conventional MPI systems utilize a sensitive point which is scanned over a volume to construct a 3D image. In some embodiments, embodiments described herein may generate 2D projection images by moving a 1D FFR within a ROI. Compared to the single sensitive point technology that is used in conventional MPI, imaging can be performed more rapidly with the 1D FFR, which may enable real-time tracking with high spatial resolution. Embodiments described herein may also be suitable for 3D projection reconstruction imaging.

In some embodiments, the magnetic material may be injected into the patient. The magnetic material may be configured to be absorbed or particularly drawn to predetermined regions within the patient's body. In such embodiments, the magnetic material within the predetermined regions of the patient (e.g., particular tissue or anatomical structure) or within the bloodstream and the magnetic material in the instrument may be distinguished based on size and/or composition of the magnetic material.

Magnetic particle imaging (MPI) concepts are described in greater detail in T. Knopp, T. M. Buzug, *Magnetic Particle Imaging: An Introduction to Imaging Principles and Scanner Instrumentation* (2012), Chapter 2: "How Magnetic Particle Imaging Works," and Chapter 3: "How to Build an MPI Scanner," in which each of the chapters is incorporated by reference in its entirety for the purpose of understanding the embodiments described herein. MPI concepts with respect to field free lines are described in greater detail in Weizenecker et al., *Magnetic Particle Imaging Using a Field Free Line*, J. Phys. D: Appl. Phys. 41 (2008) and in Knopp et al., *Field-Free Line Formation in a Magnetic Field*, J. Phys. A: Math. Theor. 43 (2010), each of which is incorporated by reference in its entirety for the purpose of understanding the embodiments described herein. MPI concepts with respect to 2D projection imaging is described in Goodwill et al., *Projection X-Space Magnetic Particle Imaging*, IEEE Transactions on Medical Imaging, Vol. 31, No. 5, May 2012, which is incorporated by reference in its entirety for the purpose of understanding the embodiments described herein. MMI systems and methods set forth herein may be based on such MPI concepts.

At least one technical effect of embodiments described herein may include improved methods or systems for imaging magnetic material within a ROI and/or tracking an instrument having magnetic material. At least one technical effect may include obtaining 3D image data of a patient and/or instrument. Another technical effect may include a MMI system that has a bi-planar C-arm geometry. Yet still another effect may include a reduction in acquisition time.

The following detailed description of various embodiments will be better understood when read in conjunction with the appended figures. To the extent that the figures illustrate diagrams of the functional blocks of the various embodiments, the functional blocks are not necessarily indicative of the division between hardware circuitry. Thus, for example, one or more of the functional blocks (e.g., modules, processing units, or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 1:
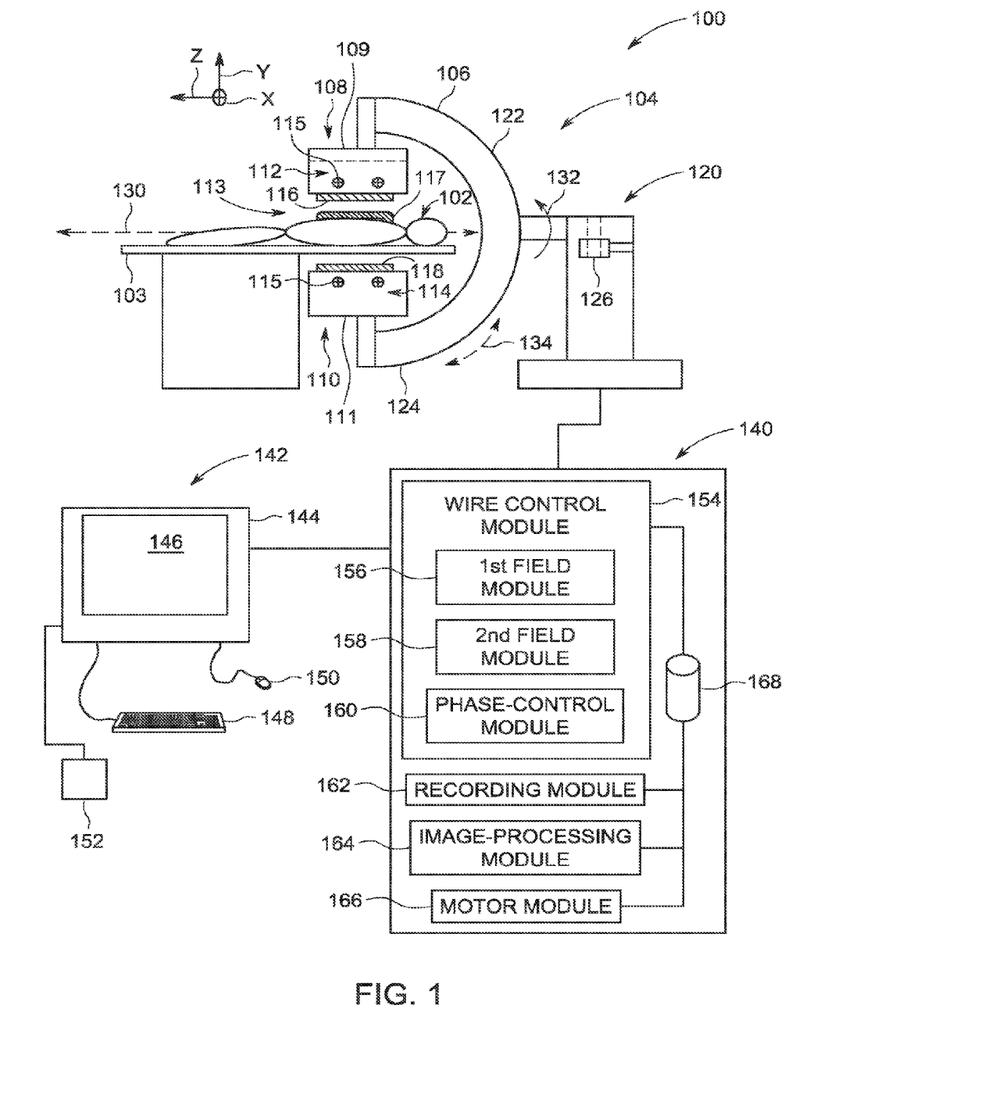
FIG. 1 illustrates a schematic block diagram of a magnetic material imaging (MMI) system in accordance with one embodiment.

FIG. 1 is a schematic diagram of a MMI system 100 formed in accordance with one embodiment. The MMI system 100 is configured to image magnetic material within an object 102. In the illustrated embodiment, the object 102 is a patient and, as such, will be referred to as the patient 102. The patient 102 may be human or an animal. However, it is understood that the object may not be human or animal in other embodiments. For example, the object may be any apparatus (e.g., luggage, containers, etc.) in which it is desired to image magnetic material within the object.

In some embodiments, the magnetic material is part of an instrument (e.g., catheter or other surgical device) that is inserted into the body of the patient 102. The MMI system 100 may be used to track the instrument. In such embodiments, the instrument may be inherently magnetic or may be modified to include the magnetic material. For example, the instrument can have magnetic particles inserted into the instrument or the instrument can be coated with magnetic particles. The magnetic particles may be characterized as superparamagnetic iron oxide particles (SPIOs). In other embodiments, the magnetic material may be a tracer or, more specifically, a substance that facilitates the imaging process. For example, the substance may include biocompatible magnetic particles that have been deposited (e.g., injected or otherwise positioned within the patient 102). Resovist® is a contrast agent that includes magnetic nanoparticles that may have a suitable magnetic moment and relaxation time for MMI. However, such nanoparticles are only examples of particles that may be suitable for MMI and other particles or materials may exist or may be developed for MMI.

As shown in FIG. 1, the MMI system 100 includes an imaging assembly or imager 104 that is configured to image the patient 102 as described herein. In the illustrated embodiment, the imaging assembly 104 has an open bi-planar configuration with a C-arm 106. However, the MMI system 100 and the imaging assembly 104 may have various configurations and embodiments that are not limited to the bi-planar configuration shown in FIG. 1. As shown, the imaging assembly 104 includes first and second field-generating units 108, 110 (also referred to as field generators) that are spaced apart from each other. The first and second field-generating units 108, 110 include first and second assembly housings 109, 111, respectively. The space between the field-generating units 108, 110 (or the assembly housing 109, 111) may be sufficient for the patient 102 and a table 103 supporting the patient 102 to be positioned therebetween.

Each of the field-generating units 108, 110 includes first and second arrays 112, 114 of elongated wire segments 115, respectively, which are held by the first and second assembly housings 109, 111. Optionally, the field-generating units 108, 110 may include permanent magnets in addition to the wire segments 115. The field-generating units 108, 110 and, particularly, the wire segments 115 of the field-generating units 108, 110 are configured to generate magnetic fields for imaging the patient 102 through MMI.

The imaging assembly 104 also includes a detection assembly 113 that, in some embodiments, may be referred to as a receiver or receiving assembly. In the illustrated embodiment, the detection assembly 113 includes recording coils 116-118. In other embodiments, the detection assembly 113 may include other components for detecting magnetization changes, such as an antenna or magnetometer (e.g., flux-gate, hall probe, atomic magnetometer, diamond magnetometer, magneto-resistive sensor, giant magneto-resistive sensor, anisotropic magneto-resistive sensor, superconducting quantum interference device (SQUID), and the like). The recording coils 116-118 are positioned relative to the patient 102 to detect changes in magnetization of magnetic material located in the patient 102. For example, the recording coils 116-118 may detect an induced voltage that is caused by the changes in magnetization. In other embodiments, a change in current may be detected. In the illustrated embodiment, the recording coils 116, 118 are attached to the field-generating units 108, 110, respectively, but the recording coils 116, 118 may have other locations relative to the patient 102. Each of the recording coils 116, 118 may have a fixed position that is separate from the field-generating units 108, 110. For example, the recording coil 117 extends along a side of the patient 102 and the table 103. In alternative embodiments, one or more of the recording coils 116-118 may be included in the field-generating units.

Optionally, the imaging assembly 104 includes a positioning system 120 that moves the field-generating units 108, 110 relative to the patient 102. For instance, the positioning system 120 may include first and second arms 122, 124 that support the first and second field-generating units 108, 110, respectively. The arms 122, 124 in the illustrated embodiment are shaped to form a C-arm geometry, although other geometries may be used. The positioning system 120 may include a mechanical device, such as a motor 126, for rotating the arms 122, 124 and, hence, the field-generating units 108, 110 about an examination axis 130. In other embodiments, the mechanical device may be similar to a drafting light that enables a person to manually move the arms 122, 124. As shown in FIG. 1, the examination axis 130 extends longitudinally along a length or height of the patient 102. The arms 122, 124 may be rotated as indicated by the arrow 132 such that the arms 122, 124 rotate about the examination axis 130. In other embodiments, the arms 122, 124 may be rotated about an axis that intersects the examination axis 130. As shown by the arrow 134, the arms 122, 124 may be moved within a plane defined by the page (e.g., a plane that coincides with or is parallel to the examination axis 130). Moreover, in some embodiments, the positioning system 120 may be shifted or moved along the ground to reposition the detection assembly 120 with respect to the patient 102. Yet still in other embodiments, the table 103 may be part of the positioning system and be configured to move along the examination axis 130.

As shown, the imaging assembly 104 is operably connected (e.g., with physical wires or wirelessly connected) to a computing system 140. The computing system 140 is operably connected to a user interface 142 that enables an operator to control at least some of the operations of the MMI system 100. The user interface 142 may include hardware, firmware, software, or a combination thereof that enables an individual (e.g., an operator) to directly or indirectly control operation of the MMI system 100 and the various components thereof. As shown, the user interface 142 includes a display device 144 having a display area 146. In some embodiments, the user interface 142 may also include one or more input devices, such as a physical keyboard 148, mouse 150, and/or touchpad 152.

In some embodiments, the display device 144 may include a touch-sensitive display (e.g., touchscreen) that can detect a presence of a touch from the operator on the display area 146 and can also identify a location of the touch in the display area 146. The touch may be applied by, for example, at least one of an individual's hand, glove, stylus, or the like. As such, the touch-sensitive display may also be characterized as an input device that is configured to receive inputs from the operator. The display device 144 may also communicate information to the operator by displaying the information to the operator or by displaying MMI images to the operator. The MMI images may be combined with other types of images, such as x-ray images. The display device 144 is configured to present information to the operator during the imaging session.

The computing system 140 may include a plurality of modules. The modules may be part of a single processing unit (e.g., processor) or distributed across multiple processing units (e.g., multi-processor). The computing system 140 is configured to control operation of the MMI system 100 and, more specifically, the imaging assembly 104. To this end, the computing system 140 and the modules may be configured to execute one or more predetermined algorithms. For example, the computing system 140 may include a wire-control module 154 that is configured to control operation of the arrays 112, 114 of the wire segments 115. The wire-control module 154 may include sub-modules, such as a first-field module 156, a second-field module 158, and a phase-control module 160. The first-field module 156 may be used to control the current through the array 112 of the field-generating unit 108, and the second-field module 158 may be used to control the current through the array 114 of the field-generating unit 110. The phase-control module 160 may communicate with the first-field and second-field modules 156, 158 to control the current through the arrays 112, 114. In some embodiments, the phase-control module 160 may directly control the current (e.g., the phase and amount of current) through the arrays 112, 114. The flow of current through the wire segments 115 may be pursuant to one or more algorithms.

The computing system 140 also includes a recording module 162. The recording module 162 is operably connected to the detection assembly 113 (e.g., recording coils 116-118) and is configured to receive data from the detection assembly 113 that represents detection of magnetization changes. For example, the data may represent a voltage induced in the recording coils by the changes in magnetization within a volume of the patient or change in current. The recording module 162 may also control operation of the recording coils 116-118 to facilitate detection of the magnetization changes.

The computing system 140 also includes an image-processing module 164. The image-processing module 164 receives image data (e.g., MMI data from the recording module 162) and processes the image data. For instance, the image-processing module 164 may include one or more components for filtering and/or amplifying the signals to generate the images (e.g., projections). As one example, the image-processing module 164 may process the MMI data to generate image frames of the magnetic material, such as an instrument or anatomical structure of the patient. The image-processing module 164 may communicate with the display device 144 to display the MMI images. In some cases, the images obtained by the imaging assembly 104 are 2D projections. The 2D projections may be processed into 2D images and/or processed into 3D images by acquiring a series of 2D images at various projection angles.

In some embodiments, the image-processing module 164 may combine the MMI data with data from other imaging modalities, such as x-ray data, ultrasound data, MRI data, and the like. The image-processing module 164 may process the data from multiple modalities to form a combined or composite image. For example, the combined image may show an anatomical structure as captured through X-ray imaging and also show an instrument as captured through MMI. In some cases, the instrument may appear to be overlaid with the anatomical structure. In other embodiments, the image-processing module 164 may process the data separately and display the images on the display device 144 as separate images (e.g., side-by-side).

A motor module 166 may also be part of the computing system 140. The motor module 166 may command the positioning system 120 to move the field-generating units 108, 110 in accordance with a predetermined protocol (e.g., algorithm). The positioning system 120 may communicate with the wire-control module 154 and/or the recording module 162 to image the patient 102 in accordance with the protocol. For example, the motor module 166 may command the positioning system 120 to rotate about the examination axis 131 at a designated speed so that the imaging assembly 104 can capture certain MMI images of the patient 102. Also shown in FIG. 1, each of the modules may utilize or communicate with a memory 168. In some embodiments, the image data may be stored and communicated to remote systems.

Figure 2:
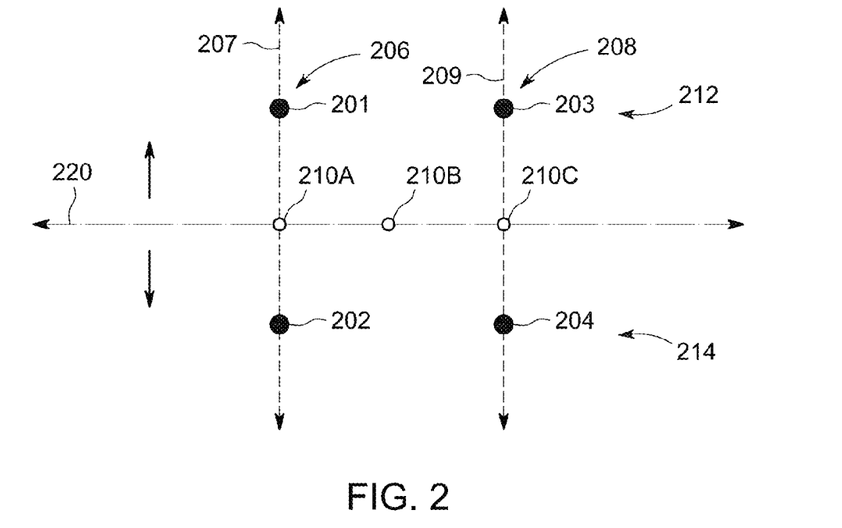
FIG. 2 illustrates end views of wire segments in accordance with one embodiment that are configured to generate a 1D field-free region (FFR).

FIG. 2 illustrates an arrangement of wire segments 201-204 in accordance with one embodiment that may be incorporated with the MMI system 100 (FIG. 1). In the illustrated embodiment, the wire segments 201-204 extend into and out of the page and appear parallel to each other. However, in other embodiments, one or more of the wire segments 201-204 may be non-parallel with respect to the others. For example, the wire segments 201, 202 may be parallel to each other and form a first segment pair 206. The wire segments 201, 202 of the segment pair 206 may coincide with a segment plane 207. The wire segments 203, 204 may be parallel to each other and form a second segment pair 208, and the wire segments 203, 204 of the segment pair 208 may coincide with a segment plane 209.

The wire segments 201, 203 may be part of a first array 212 of wire segments and/or part of a first field-generating unit, such as the field-generating unit 108 (FIG. 1). The wire segments 202, 204 may be part of a second array 214 of wire segments and/or part of a second field-generating unit, such as the field-generating unit 110 (FIG. 1). The first and second arrays 212, 214 are spaced apart from each other. As described herein, a ROI of a patient may be located between the first and second arrays 212, 214.

During operation, current flowing through each of the wire segments 201-204 generates a respective magnetic field. A strength of the magnetic field decreases as a distance from the wire segment increases or as the amount of current changes in the wire segment. When arranged in a designated manner relative to one another, the respective magnetic fields may combine together to generate a sensitive low-field region that has, for example, a magnetic field substantially equal to zero. In particular, the wire segments 201-204 are configured to generate a 1D FFR 210. The 1D FFR 210 is referenced at different positions as 210A, 210B, 210C. The phase of the current in segment pair 206 may be different than the phase of the current in segment pair 208 such that the 1D FFR 210 is moved along an imaging plane 220. More specifically, the 1D FFR may be located at 210A at time $t_0$, the 1D FFR may be located at 210B at time $t_1$, which is after $t_0$, and the 1D FFR may be located at 210C at time $t_2$, which is after $t_1$.

The imaging plane 220 represents the planar area or space that the 1D FFR 210 may move through due to the magnetic fields changing as a function of time. In the illustrated embodiment, the imaging plane 220 intersects the segment planes 207, 209. In certain embodiments, the imaging plane 220 is orthogonal to (e.g., perpendicular to) the segment planes 207, 209. In the illustrated embodiment, a magnitude of the current flowing through the first array 212 is substantially equal to a magnitude of the current flowing through the second array 214 such that the imaging plane 220 is equidistant from the wire segments 201, 203 and the wire segments 202, 204.

However, the magnitudes may be changed such that the imaging plane 220 moves closer to or further away from either of the first and second arrays 212, 214. For each wire segment 201-204, the respective magnetic field generated by the corresponding wire segment decays as a function of distance from a center of the corresponding wire segment. This property may be utilized to control movement of the 1D FFR. For example, if the magnitude of the current flowing through the first array 212 was increased and/or the magnitude of the current flowing through the second array 214 was decreased the 1D FFR may move closer to the second array 214.

By way of example, in one embodiment, the difference in phase for alternating current flowing into and out of the page along the parallel wire segments 201-204 may be offset by 90 degrees between segment pairs 206 and 208. At time t=0, current may exist within the wire segments 201 and 202, but not within the wire segments 203 and 204. At t=0, the 1D FFR extends along the segment plane 207 and parallel to wire segments 201 and 202. The relative position of the FFR with respect to wire segments 201 and 202 may be based on a relative amplitude of the current between the wire segments 201 and 202. As time increases, the current in the segment pair 206 decreases as the current in the segment pair 208 increases and the 1D FFR moves to a position between the segment planes 207 and 209. The 1D FFR continues to move until one quarter of a cycle (T/4) when there is no current in the wire segment 206 and the wire segment 208 has a maximum amount of current. At this time, the 1D FFR may exist within the segment plane 209. From t=T/4 to t=T/2, the 1D FFR may not exist within the ROI. At time t=T/2, the wire segment 206 again has a designated amount of current and the 1D FFR exists within the segment plane 207. From t=T/2 to t=3/4T, the 1D FFR again sweeps from the segment plane 207 to the segment plane 209. From t=3/4T to t=T, the 1D FFR is again absent in the ROI.

Figure 3:
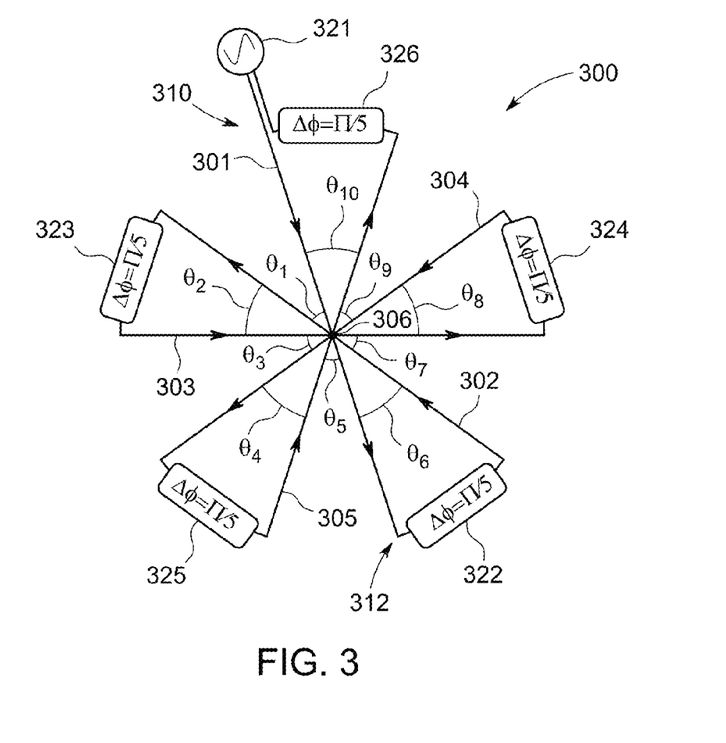
FIG. 3 illustrates an array of wire segments that may be used to generate a 1D FFR.

FIG. 3 is a plan view of an array 300 of elongated wire segments 301-305. In some embodiments, the wire segments 301-305 are part of common circuit in which the current flowing through the wire segment 301 also flows through the wire segments 302-305. As shown, the wire segments 301-305 form a hub-and-spoke or asterisk configuration. More specifically, each of the wire segments 301-305 is substantially linear and extends across other wire segments at a pivot-point region 306. With respect to the wire segment 301 only, each of the wire segments 301-305 may extend between a first 310 and a second end 312. The first and second ends 310, 312 may be dimensioned to have at least a designated minimum value so that the resulting 1D FFR has a sufficient length for imaging as described herein. In particular embodiments, lengths of the wire segments 301-305 may be substantially equal as shown in FIG. 3.

The array 300 may also include intermediate circuit elements 321-325. The circuit elements 321-325 may join the wire segments 301-305 along a perimeter of the array 300. For example, the circuit element 321 may be an alternating current (AC) source. In the illustrated embodiment, the circuit elements 322-325 may be active or passive phase control elements that are configured to change the phase of the current flowing through the wire segments 301-305. For example, the circuit element 322 electrically joins the wire segment 301 and the wire segment 302; the circuit element 323 electrically joins the wire segment 302 and the wire segment 303; the circuit element 324 electrically joins the wire segment 303 and the wire segment 304; the circuit element 325 electrically joins the wire segment 304 and the wire segment 305; and the circuit element 326 electrically joins the wire segment 305 and the wire segment 301 or the circuit element 321.

For each case, the intermediate circuit element may change a phase of the incoming current so that the phase of the outgoing current is offset by a predetermined value. In the illustrated embodiment, each of the wire segments 301-305 is offset by $\pi/5$ with respect to the adjacent wire segments. For example, the phase of the wire segment 302 is $\pi/5$ greater than the phase of the wire segment 301 and $\pi/5$ less than the phase of the wire segment 303. Accordingly, the phase in each wire segment (i.e., spoke) may be varied by using multiple circuit elements or independent signal generators and amplifiers for each channel. This feature may be similar to varying the phase in parallel transmit systems for MRI.

Accordingly, the difference in phase of the current flowing through adjacent wire segments may be equal to an angle $\theta$ between the adjacent wire segments. In particular embodiments, the wire segments 301-305 are positioned relative to one another such that the angles $\theta_{1-10}$ between adjacent wire segments are equal to each other. In other words, the wire segments 301-305 may be equally spaced apart. In the illustrated embodiment, the common angle is 36° or $\pi/5$ radians. It is understood, however, a different number of wire segments and/or different angles between the adjacent wire segments may be used.

Figure 4:
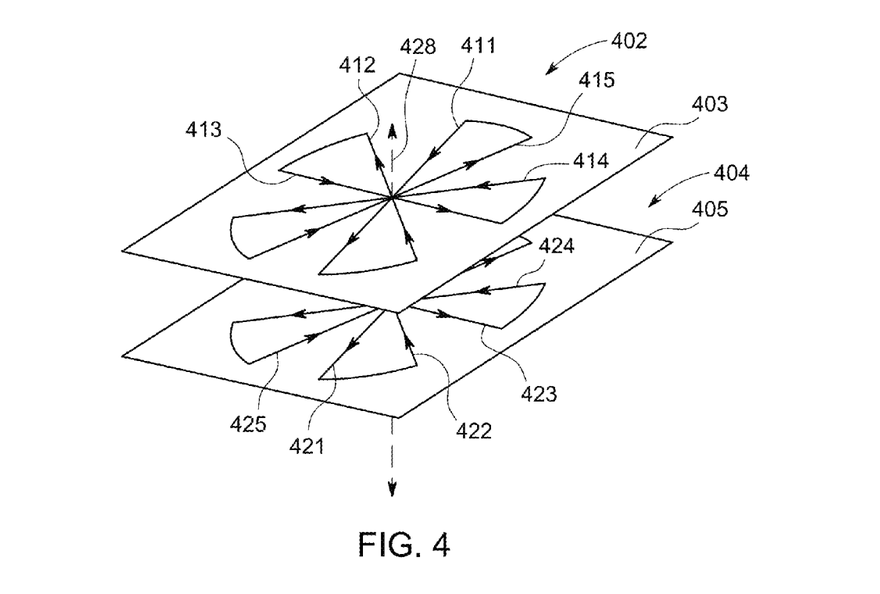
FIG. 4 illustrates two opposing arrays of wire segments that are configured to generate a movable 1D FFR therebetween.

FIG. 4 shows first and second arrays 402, 404 of wire segments that are arranged along respective array planes 403, 405. When the first and second arrays 402, 404 are incorporated with an MMI system, such as the MMI system 100 (FIG. 1), a patient may be positioned between the first and second arrays 402, 404. The first array 402 includes wire segments 411-415 and the second array 404 includes wire segments 421-425. The wire segments 411-415 are positioned substantially along the array plane 403, and the wire segments 421-425 are positioned substantially along the array plane 405. As similarly described in reference to FIG. 2, the wire segments 411-415 are oriented to extend parallel to wire segments 421-425, respectively. For example, the wire segment 411 is oriented to extended parallel to the wire segment 421 to form a segment pair in which the wire segments 411, 421 coincide along a common plane (e.g., segment plane) (not shown). The wire segments 412-415 may form corresponding segment pairs with the wire segments 422-425, respectively.

Similar to the array 300 (FIG. 3), the arrays 402, 404 are configured to change or modify the phases of the current flowing through the wire segments to generate and move the 1D FFR. For example, current flowing through the wire segments of each segment pair may have substantially equal phases, but the currents of adjacent segment pairs may have a designated phase offset. In particular embodiments, the designated phase offset is substantially equal to $\pi/N$, wherein N is a number of segment pairs (or a number of wire segments in a single array). In the illustrated embodiment, N is equal to five (5). As such, the designated phase offset between adjacent segment pairs (or the wire segments of an array) is $\pi/5$. However, it is understood that N may have any one of a number of values. For instance, N may be equal to eight (8) or ten (10).

In such embodiments, a rotating 1D FFR may be provided that rotates based on the positions of the wire segments 411-415, 421-425 with respect to one another and the different phases of the current flowing through the wire segments. More specifically, the 1D FFR may rotate about an axis of rotation 428. The 1D FFR rotates within an imaging plane (not shown) that is substantially parallel to the array planes 403, 405. As such, the axis of rotation 428 intersects and is substantially orthogonal (e.g., perpendicular) to each of the array planes 403, 405 and the imaging plane.

As described herein, the imaging plane may be equally spaced apart from the array planes 403, 405 or, alternatively, may be positioned closer to (or further from) either of the array planes 403, 405. Movement of the imaging plane may be accomplished mechanically, or by changing a magnitude of the current in the arrays 402, 404. In other embodiments, a separate magnetic field may be generated (e.g., by a separate electromagnetic assembly).

Figure 5:
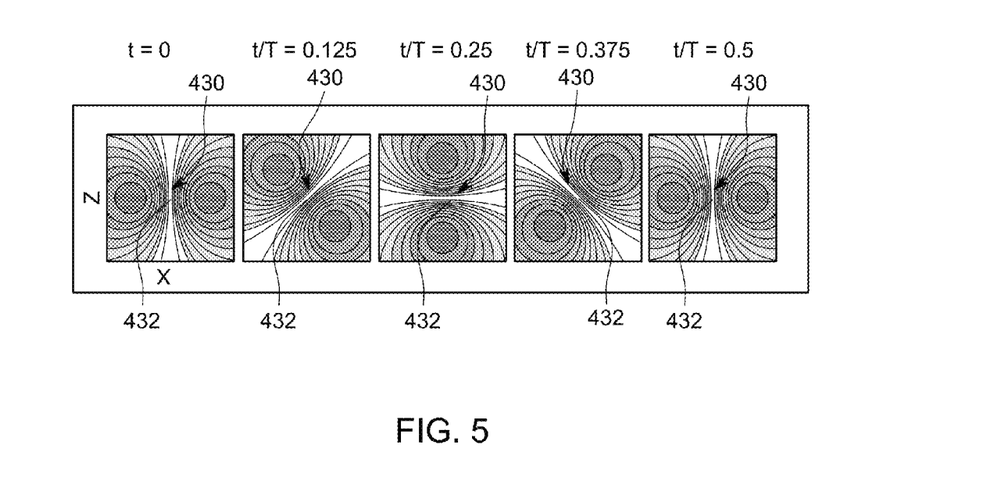
FIG. 5 is a series of images that illustrate rotational movement of a 1D FFR about a pivot-point region in accordance with one embodiment.

FIG. 5 includes a series of images that illustrate a rotating 1D FFR 430 generated by a bi-planar MMI imaging system having eight segment pairs. FIG. 5 shows five different images of the 1D FFR 430 over the course of half of a period (T) of the AC drive current. The 1D FFR 430 is indicated as a substantially white linear region. As shown, the 1D FFR 430 rotates about a pivot-point region 432 approximately 180 degrees between the first image (t=0) and the last image (t/T=0.5). The 1D FFR may move continuously through the imaging plane. During this time period, a 2D slice of the ROI may be obtained.

FIG. 5 also shows a signal-void region 432 that is located along the axis of rotation of the 1D FFR. The signal-void region 432 represents a limited point or portion of the ROI that may not change in magnetization. As such, image data may not be able to be obtained at the signal-void region 432. However, in some embodiments, changes in magnetization at the signal-void region 432 may be obtained through high frequency, low amplitude modulation of the magnetic field. For example, changes in magnetization at the signal-void region 432 may be obtained by applying a lower amplitude, higher frequency current to one of the arrays with the effect of rapidly modulating the 1D FFR in a direction perpendicular to the array planes (e.g., along the axis of rotation). As such, changes in magnetization at the signal-void region 432 may be obtained.

Figure 6:
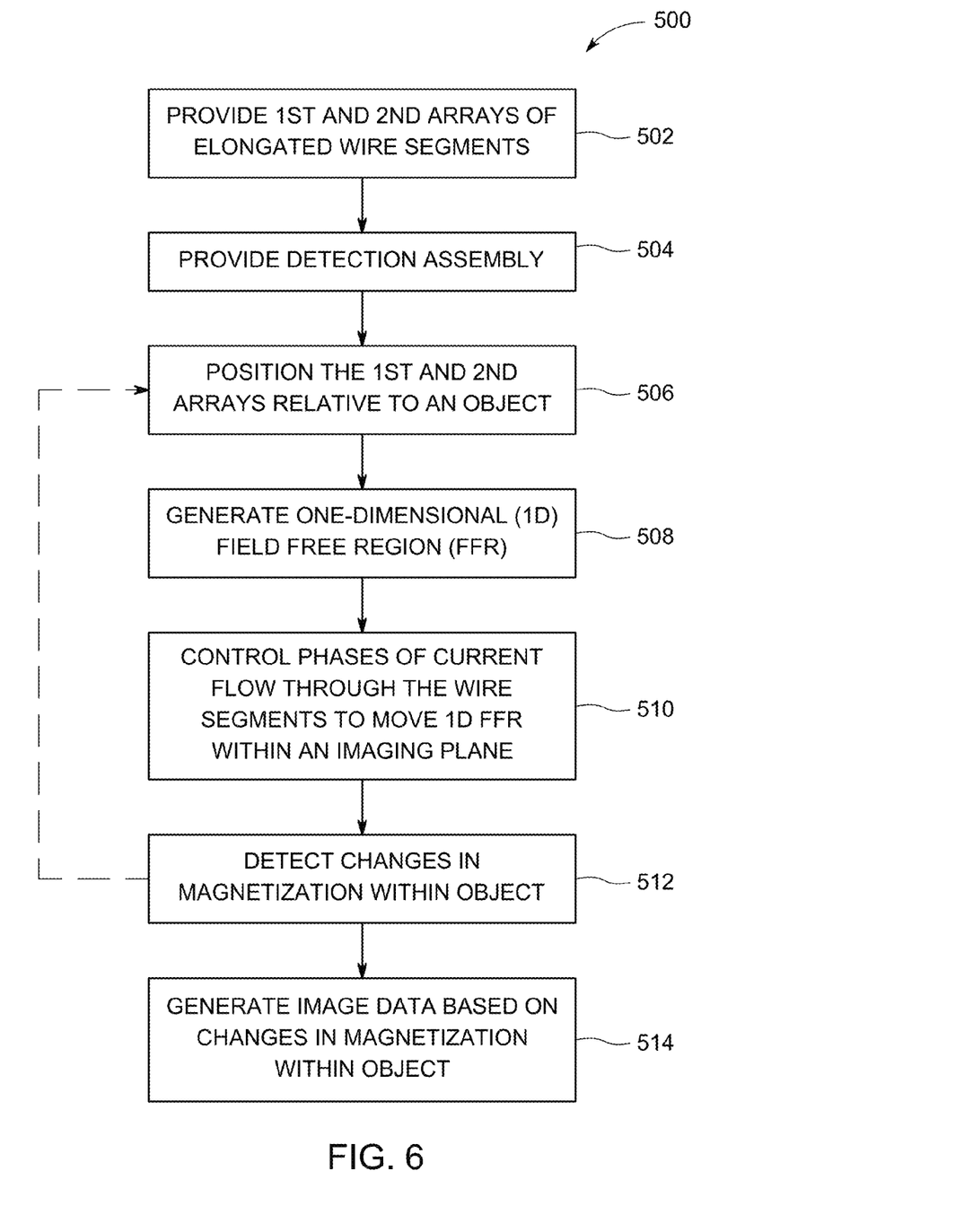
FIG. 6 is a flowchart illustrating a method of imaging a region-of-interest (ROI) with MMI.

FIG. 6 illustrates a method 500 of imaging a ROI in a patient through MMI. The method 500 includes providing (at 502) a first array of elongated wire segments and a second array of elongated wire segments. The wire segments of the first and second arrays may extend substantially parallel to an imaging plane that is positioned between the first and second arrays. For example, the wire segments of the first and second arrays may be similar to the wire segments 411-415, 421-425 (FIG. 4). The wire segments of the first array may be non-parallel with respect one another, and the wire segments of the second array may be non-parallel with respect one another. For example, the wire segments of each array may substantially intersect each other at a pivot-point region. At the pivot-point region, the wire segments may be redirected or bent so that the wire segments move around the other wire segments.

The method 500 may also include providing (at 504) a detection assembly. The detection assembly may be similar to the detection assembly 113 (FIG. 1) and include recording coils or other components for detecting magnetization changes (e.g., an antenna or magnetometer). The providing (at 504) may include positioning the detection assembly relative to the object to detect changes in magnetization of magnetic material located in the object.

The method 500 also includes positioning (at 506) the first and second arrays of wire segments relative to an object to be imaged. As set forth herein, the object may be a patient in particular embodiments. The first and second arrays may be positioned relative to an ROI of the patient, such as a particular anatomical structure (e.g., heart, tissue, organ, head, abdomen, and the like). For example, the first and second arrays may be positioned such that the first and second arrays directly oppose each other with the object therebetween. In some cases, the positioning (at 506) may include re-positioning the first and second arrays to obtain a subsequent image that shows a different angle/view of the ROI than the prior image.

The method 500 may also include generating (at 508) a 1D FFR. The dimensions and position of the 1D FFR may be based on current flowing through the wire segments of the first and second arrays and based on positions of the wire segments relative to one another. For example, the longer the wire segments, the longer the 1D FFR can be generated. The method also includes controlling (at 510) phases of the current flowing through the wire segments to move the 1D FFR within the imaging plane. As described herein, each of the wire segments may have a phase offset with respect to adjacent wire segments.

The method 500 may also include detecting (at 512) changes in magnetization of magnetic material located proximate to the 1D FFR in a ROI and, optionally, generating (at 514) image data of the ROI based on the changes in magnetization. In some embodiments, 2D projections may be obtained and the 2D projections may be processed to generate 3D images. In other embodiments, 3D projection reconstruction imaging may be performed.

It is noted that the MMI systems described herein may be used in conjunction with other imaging systems. For instance, the MMI system can be part of a multi-modality imaging system that includes an imaging system of another modality. Examples of such other imaging systems include x-ray fluoroscopy, nuclear imaging, a magnetic resonance imaging (MRI) system, computed tomography (CT) system, positron emission tomography (PET) system, a PET/CT system, and single photon emission computed tomography (SPECT) system.

In one embodiment, a magnetic material imaging (MMI) system is provided that includes a first array of elongated wire segments that extend substantially parallel to an imaging plane. The imaging plane is configured to extend through a region-of-interest (ROI) of an object. The MMI system also includes a second array of elongated wire segments that extend substantially parallel to the imaging plane. The first and second arrays of wire segments are spaced apart with the imaging plane therebetween. The first and second arrays of wire segments form segment pairs. Each segment pair includes a wire segment of the first array and a wire segment of the second array, wherein the wire segments substantially coincide along a segment plane. The MMI system also includes a phase-control module that is configured to control a flow of current through the wire segments of the segment pairs to generate and move a one-dimensional field free region (1D FFR) within the imaging plane. Each of the segment pairs has a time-varying phase that is offset with respect to the phase of at least one other segment pair. The MMI system also includes a detection assembly positioned relative to the ROI to detect changes in magnetization of magnetic material located proximate to the 1D FFR.

In one aspect, the wire segments of the first array are non-parallel with one another, and the wire segments of the second array are non-parallel with one another.

In another aspect, the wire segments of the first and second arrays are arranged such that the 1D FFR rotates about an axis of rotation. For example, the axis of rotation may be orthogonal to the imaging plane.

In another aspect, the wire segments of the first array are non-parallel with one another and the wire segments of the second array are non-parallel with one another. The respective phases of the current flowing through the wire segments of adjacent segment pairs may be offset by a value equal to an angle between the corresponding adjacent segment pairs.

In another aspect, the segment pairs are positioned relative to one another such that the angles existing between the adjacent segment pairs are substantially equal.

In another aspect, the system may include an image-processing module configured to receive image data from the detection assembly. The image data may be based on measurements of the changes in magnetization. In some embodiments, the image-processing module is configured to generate 3D images from the image data. In particular embodiments, the magnetic material is part of an instrument and the changes in magnetization within the ROI are caused by the magnetic material of the instrument. The image-processing module may be configured to generate a representation of the instrument within the ROI.

In another embodiment, a magnetic material imaging (MMI) system is provided that includes a first field-generating unit having an assembly housing and a first array of elongated wire segments held by the assembly housing of the first field-generating unit. The MMI system also includes a second field-generating unit having an assembly housing and a second array of elongated wire segments held by the assembly housing of the second field-generating unit. The first and second arrays of wire segments extend substantially parallel to a common imaging plane that extends through a region-of-interest (ROI) of an object. The first and second field-generating units are located on opposite sides of the imaging plane. The MMI system also includes a phase-control module that is configured to control a flow of current through the wire segments of the first and second arrays to generate and move a one-dimensional field free region (1D FFR) within the imaging plane. Each of the wire segments has a time-varying phase that is offset with respect to the phase of at least one other wire segment. The MMI system also includes a detection assembly positioned relative to the ROI to detect changes in magnetization of magnetic material located proximate to the 1D FFR.

In one aspect, the wire segments of the first array are non-parallel with one another, and the wire segments of the second array are non-parallel with one another.

In another aspect, the MMI system may include a positioning system having first and second arms coupled to the first and second field-generating units, respectively, wherein the first and second arms form an open bi-planar C-arm geometry.

In yet another embodiment, a method of imaging a region-of-interest (ROI) in a patient through magnetic material imaging (MMI) is provided. The method includes providing a first array of elongated wire segments and a second array of elongated wire segments. The wire segments of the first and second arrays extend substantially parallel to an imaging plane that is positioned between the first and second arrays. The method also includes generating a 1D FFR based on current flowing through the wire segments of the first and second arrays and based on positions of the wire segments relative to one another. The method also includes controlling phases of the current flowing through the wire segments to move the 1D FFR within the imaging plane. The method also includes detecting changes in magnetization of magnetic material located proximate to the 1D FFR in a ROI of a patient.

In one aspect, the wire segments of the first and second arrays are arranged such that the 1D FFR rotates about an axis of rotation.

In another aspect, the current flowing through adjacent wire segments of a common array has a phase offset that is equal to the angle between them.

In another aspect, the method includes generating 3D images from the image data.

In accordance another embodiment, a non-transitory computer readable medium for imaging a region-of-interest (ROI) in a patient through magnetic material imaging (MMI) is provided. The computer readable medium includes instructions to command the processor to generate a 1D FFR based on current flowing through wire segments of first and second arrays and based on positions of the wire segments relative to one another. The computer readable medium also includes instructions to command the processor to control phases of the current flowing through the wire segments to move the 1D FFR within the imaging plane. The computer readable medium may also include instructions to command the processor to detect changes in magnetization of magnetic material located proximate to the 1D FFR in a ROI of a patient.

The systems (e.g., the computing system 140) described herein can include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. These devices may be off-the-shelf devices that perform the operations described herein from the instructions described above. Additionally or alternatively, one or more of these devices may be hard-wired with logic circuits to perform these operations.

Moreover, the block diagrams of embodiments herein illustrate various blocks labeled "module." It is to be understood that the modules represent circuit modules that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hard wired to perform the functions described herein. Optionally, the hardware may include electronic circuits that include and/or are connected to one or more logic-based devices, such as microprocessors, processors, controllers, or the like. Optionally, the modules may represent processing circuitry such as one or more field programmable gate array (FPGA), application specific integrated circuit (ASIC), or microprocessor. The circuit modules in various embodiments may be configured to execute one or more algorithms to perform functions described herein. The one or more algorithms may include aspects of embodiments disclosed herein, whether or not expressly identified in a flowchart or a method.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "comprises," "including," "includes," "having," or "has" an element or a plurality of elements having a particular property may include additional such elements not having that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A magnetic material imaging (MMI) system comprising:
   a first array of elongated wire segments that extend substantially parallel to an imaging plane, the imaging plane configured to extend through a region-of-interest (ROI) of an object;
   a second array of elongated wire segments that extend substantially parallel to the imaging plane, the first and second arrays of wire segments being spaced apart with the imaging plane therebetween, wherein the first and second arrays of wire segments form segment pairs, each segment pair including a wire segment of the first array and a wire segment of the second array that substantially coincide along a segment plane;
   a phase-control circuit configured to control a flow of current through the wire segments of the segment pairs to generate and move a one-dimensional field free region (1D FFR) within the imaging plane, the 1D FFR being an elongated sensitive low-field region within the imaging plane, wherein each of the segment pairs has a time-varying phase that is offset with respect to the phase of at least one other segment pair; and
   a detection assembly including recording coils that are positioned relative to the ROI to detect changes in magnetization of magnetic material located proximate to the 1D FFR.

2. The MMI system of claim 1, wherein the wire segments of the first array are non-parallel with one another and the wire segments of the second array are non-parallel with one another.

3. The MMI system of claim 1, wherein the wire segments of the first and second arrays are arranged such that the 1D FFR rotates about an axis of rotation.

4. The MMI system of claim 3, wherein the axis of rotation is orthogonal to the imaging plane.

5. The MMI system of claim 1, wherein the wire segments of the first array are non-parallel with one another and the wire segments of the second array are non-parallel with one another, wherein the respective phase of the current flowing through the wire segments of adjacent segment pairs is offset by a value equal to an angle between the corresponding adjacent segment pairs.

6. The MMI system of claim 5, wherein the segment pairs are positioned relative to one another such that the angles existing between the adjacent segment pairs are substantially equal.

7. The MMI system of claim 1, further comprising an image processor configured to receive image data from the detection assembly, the image data being based on measurements of the changes in magnetization.

8. The MMI system of claim 7, wherein the image processor is configured to generate 3D images from the image data.

9. The MMI system of claim 7, wherein the magnetic material is part of an instrument, the changes in magnetization within the ROI being caused by the magnetic material of the instrument, the image processor configured to generate a representation of the instrument within the ROI.

10. A magnetic material imaging (MMI) system comprising:
    a first field-generating unit including an assembly housing and a first array of elongated wire segments held by the assembly housing of the first field-generating unit;
    a second field-generating unit including an assembly housing and a second array of elongated wire segments held by the assembly housing of the second field-generating unit, wherein the first and second arrays of wire segments extend substantially parallel to a common imaging plane that extends through a region-of-interest (ROI) of an object, the first and second field-generating units being located on opposite sides of the imaging plane;
    a phase-control circuit configured to control a flow of current through the wire segments of the first and second arrays to generate and move a one-dimensional field free region (1D FFR) within the imaging plane, the 1D FFR being an elongated sensitive low-field region within the imaging plane, wherein each of the wire segments has a time-varying phase that is offset with respect to the phase of at least one other wire segment; and
    a detection assembly including recording coils that are positioned relative to the ROI to detect changes in magnetization of magnetic material located proximate to the 1D FFR.

11. The MMI system of claim 10, wherein the wire segments of the first array are non-parallel with one another and the wire segments of the second array are non-parallel with one another.

12. The MMI system of claim 10, further comprising a positioning system having first and second arms coupled to the first and second field-generating units, respectively, wherein the first and second arms form an open bi-planar C-arm geometry.

13. The MMI system of claim 10, wherein the wire segments of the first and second arrays are arranged such that the 1D FFR rotates about an axis of rotation.

14. The MMI system of claim 10, wherein the wire segments of the first array are non-parallel with one another and the wire segments of the second array are non-parallel with one another, the first and second arrays of wire segments forming segment pairs in which each segment pair includes a wire segment of the first array and a wire segment of the second array that substantially coincide along a segment plane, wherein the respective phase of the current flowing through the wire segments of adjacent segment pairs is offset by a value equal to an angle between the corresponding adjacent segment pairs.

15. The MMI system of claim 10, further comprising an image processor configured to receive image data from the detection assembly, the image data being based on measurements of the changes in magnetization.

16. The MMI system of claim 15, wherein the image processor is configured to generate 3D images from the image data.

17. A method of imaging a region-of-interest (ROI) in a patient through magnetic material imaging (MMI), the method comprising:
    providing a first array of elongated wire segments and a second array of elongated wire segments, the elongated wire segments of the first and second arrays extending substantially parallel to an imaging plane that is positioned between the first and second arrays;
    generating a one-dimensional field free region (1D FFR) based on current flowing through the wire segments of the first and second arrays and based on positions of the wire segments of the first and second arrays relative to one another, the 1D FFR being an elongated sensitive low-field region within the imaging plane;
    controlling phases of the current flowing through the wire segments of the first and second arrays to move the 1D FFR within the imaging plane; and
    detecting changes in magnetization of magnetic material located proximate to the 1D FFR in a ROI of a patient.

18. The method of claim 17, wherein the wire segments of the first and second arrays are arranged such that the 1D FFR rotates about an axis of rotation.

19. The method of claim 17, wherein the wire segments of the first array are non-parallel with one another and the wire segments of the second array are non-parallel with one another, wherein the respective phases of the current flowing through the wire segments of adjacent segment pairs is offset by a value equal to an angle between the corresponding adjacent segment pairs.

20. The method of claim 17, further comprising generating 3D images based on image data, the image data being based on the detected changes in magnetization.

* * * * *